US006408683B2

United States Patent
Bahia et al.

(10) Patent No.: US 6,408,683 B2
(45) Date of Patent: *Jun. 25, 2002

(54) LABORATORY ASPHALT STABILITY TEST AND APPARATUS

(75) Inventors: Hussain U. Bahia; Huachun Zhai, both of Madison, WI (US)

(73) Assignee: Wisconsin Alumni Research Foundation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/332,626

(22) Filed: Jun. 14, 1999

Related U.S. Application Data

(60) Provisional application No. 60/089,217, filed on Jun. 15, 1998.

(51) Int. Cl.[7] ............................ G01N 11/00; C08L 95/00
(52) U.S. Cl. .................. 73/54.01; 73/54.37; 106/273.1; 524/68
(58) Field of Search ............................ 73/54.01, 54.07, 73/54.14, 54.28, 54.33, 54.37, 54.39, 864.35, 864.73, 864.11; 106/273.1, 274, 279, 280; 524/68, 62, 226, 71; 208/112, 86

(56) References Cited

U.S. PATENT DOCUMENTS

| | | | | |
|---|---|---|---|---|
| 3,956,001 A | * | 5/1976 | Pitchford | 106/273.1 |
| 3,960,585 A | * | 6/1976 | Gaw | 106/274 |
| 4,229,337 A | * | 10/1980 | Brenner | 524/226 |
| RE31,555 E | * | 4/1984 | Garren et al. | 73/864.11 |
| 4,675,097 A | * | 6/1987 | Patel et al. | 208/112 |
| 4,846,957 A | * | 7/1989 | Johnson et al. | 208/86 |
| 5,171,891 A | * | 12/1992 | Masilamani et al. | 562/411 |
| 5,336,705 A | * | 8/1994 | Gorbaty et al. | 524/68 |
| 5,434,334 A | * | 7/1995 | Lomasney et al. | 588/20 |
| 5,549,744 A | * | 8/1996 | Olga et al. | 106/274 |
| 5,627,225 A | * | 5/1997 | Gorbaty et al. | 524/71 |
| 5,719,215 A | * | 2/1998 | Liang et al. | 524/62 |
| 5,749,953 A | * | 5/1998 | Doyle | 106/273.1 |
| 5,766,333 A | * | 6/1998 | Lukens | 106/280 |
| 5,775,546 A | * | 7/1998 | Buehler | 222/209 |
| 5,904,760 A | * | 5/1999 | Hayner | 106/279 |
| 5,939,474 A | * | 8/1999 | Gooswilligen et al. | 524/68 |

FOREIGN PATENT DOCUMENTS

| | | | | |
|---|---|---|---|---|
| EP | 04392321 | * | 7/1991 | C08L/95/00 |
| EP | 483043 | * | 4/1992 | G01N/9/00 |

OTHER PUBLICATIONS

AASHTO SOM, Provisional Standards, Table of Contents, Dec. 1995 ASTM D 140–93.*
AASHTO, Provisional Standards, Apr. 2000, cover sheets ASTM D 4989–90a.*
Witczak et al, Laboratory Characterization of Elvaloy™ Modified Asphalt Mixtures, Jun. 1995 Asphalt Institute, Asphalt Institute Technical Bulletin, unknown date.*

* cited by examiner

*Primary Examiner*—Hezron Williams
*Assistant Examiner*—Jay L. Politzer
(74) *Attorney, Agent, or Firm*—Craig A. Fieschko, Esq.; DeWitt Ross & Stevens S.C.

(57) ABSTRACT

An asphalt stability testing vessel includes a container, an external heater, an internal heater, an agitator assembly, a temperature controller, and at least one sampling tube. The external heater is disposed on the outside surface area of the container. The external heater is surrounded by a thermal insulator. The internal heater is located inside the container and at substantially the bottom thereof. The agitator includes a motor, a shaft, and at least one propeller. The top of the container has at least one opening for the insertion of a sampling tube. The asphalt stability testing vessel is used to prepare modified asphalt binder for numerous stability tests. The tests include external heat without agitation, internal heat with high agitation, and internal heat without agitation. The values of complex shear modulus and phase angle obtained from the modified asphalt binder are analyzed for separation and degradation.

31 Claims, 2 Drawing Sheets

LABORATORY ASPHALT STABILITY TEST AND APPARATUS

This application claims priority under 35 USC §119(e) to U.S. Provisional Patent Application 60/089,217 filed Jun. 15 1998, the entirety of which is incorporated by reference herein.

NOTICE OF UNITED STATES GOVERNMENTAL FUNDING

This invention was made with United States government support awarded by the following agencies:
National Cooperative Hwy Research Program, Grant No: NCHRP 9-10
Federal Highway Administration, Grant No.: DTFH61-95-C-00055
The United States has certain rights in this invention.

BACKGROUND OF THE INVENTION

1. Field of the Invention

The present invention relates generally to the testing of asphalt and more specifically to a laboratory asphalt stability test which is able to more thoroughly test the stability of modified asphalt binder than that of the prior art.

2. Discussion of the Prior Art

At present, the most common method for testing asphalt stability is accomplished through the use of the cigar tube test. A cigar type tube is filed with modified asphalt binder and sealed. The sealed cigar type tube is heated in an oven to 163 degrees Celsius for 2 days. The sealed cigar type tube is then frozen and cut into three sections. The top and bottom sections are heated to 163 degrees Celsius for standard testing. A drawback to the cigar tube test is that it does not take agitation of the modified asphalt binder into account. In the field modified asphalt binder is mixed before it is applied. Further, the thermal history of the modified asphalt binder is altered by freezing.

Other asphalt test methods utilize molecular analysis to determine stability. However, these methods are difficult to perform in the field because of their complexity and high cost. They also fail to account for the effects of agitation of the modified asphalt binder.

Accordingly, there is a clearly felt need in the art for a laboratory asphalt stability test which simulates the condition of modified asphalt binder under field conditions by including the effects of agitation and more closely simulating thermal treatment.

SUMMARY OF THE INVENTION

The primary objective of the present invention is to provide a laboratory asphalt stability test which simulates the condition of modified asphalt binder under field conditions by including the effects of agitation and more closely simulating thermal treatment.

According to the present invention, an asphalt stability testing vessel includes a container, an external heater, an internal heater, an agitator assembly, a temperature controller, and at least one sampling tube. The external heater is disposed on the outside surface area of the container. The external heater is surrounded by a thermal insulator such as fiberglass. The internal heater is located inside the container and at substantially the bottom thereof. A plurality of baffles are disposed vertically in the container. The agitator includes a motor, a shaft, and at least one propeller. The shaft is pivotally mounted to the top and bottom of the container. A motor is mounted to the top of the container and drives the shaft which has at least one propeller attached thereto. The temperature of the sample may be maintained by the temperature controller. The temperature controller is used to control the thermal output of the internal and external heaters. The top of the container has at least one opening for the insertion of a sampling tube.

The asphalt stability testing vessel is used to prepare modified asphalt binder for numerous stability tests. The stability test is started by heating preferably one quart of modified asphalt binder to 165 degrees celsius. The sampling tubes are pre-heated in an oven. The heated modified asphalt binder is poured into the asphalt stability testing vessel. The sampling tubes are used to extract numerous samples from the top and bottom thirds of the container after the temperature therein has stabilized to 165 degrees celsius. The contents of the sampling tubes are placed into a plurality of silicon molds. The samples are then tested with preferably a dynamic shear rheometer. Other types of rheometers may be used.

The complex shear modulus ($G^*$) is the ratio calculated by dividing the absolute value of the peak-to-peak shear stress by the absolute value of the peak-to-peak strain. The phase angle ($\delta$) is the angle in radians or degrees, between a sinusoidally applied strain and the resultant sinusoidal stress in a controlled-strain testing mode, or between the applied stress and the resultant strain in a controlled-stress testing mode.

If either the complex shear modulus ($G^*$) or the phase angle ($\delta$) in either the top or bottom samples differ by more than 20 percent, separation has occurred; new samples are tested utilizing the internal heater and high agitation in the asphalt stability testing vessel. If the complex shear modulus ($G^*$) or the phase angle ($\delta$) in either the top or bottom samples differ by less than 20 percent, no separation has occurred. If no separation occurs, the values of the top and bottom samples are averaged together and plugged into a degradation equation. If the ratio of the degradation equation is greater than 1.2 or less than 0.8, degradation has occurred; the binder is unstable. If degradation has not occurred a new sample is internally heated and subjected to high agitation, if no degradation has occurred; the binder is stable. If degradation has occurred, a new sample is internally heated without agitation. If degradation occurs, the binder is not stable. If no degradation occurs then the binder is stable only with minimum agitation.

If a sample experiences separation after external heat without agitation, a new sample is internally heated and subjected to high agitation. If separation occurs, the binder is not stable. If no separation occurs, a new sample is subjected to degradation analysis. If no degradation occurs, a new sample is internally heated without agitation. If separation occurs, the binder is stable only at high agitation. If no separation occurs, the binder is stable at minimum agitation.

If degradation occurs, a new sample is internally heated without agitation. If separation occurs, the binder is not stable. If no separation occurs, the values are subjected to degradation analysis. If degradation occurs, the binder is not stable. If no degradation occurs the binder is stable only at minimum agitation.

Microscopic evaluation may also be used to determine the amount of separation in the asphalt in the top or bottom thirds of the container. Under microscopic evaluation, polymer material is brighter than asphalt material. One way of determining separation is to compare the bright polymer spots in the top sample to that of the bottom sample. If the top sample or bottom sample has more bright polymer spots than the other sample, separation has occurred. If the amount of bright polymer spots is the same in the top and bottom samples, no separation has occurred.

Some other properties which are useful in analyzing asphalt samples are loss shear modulus, storage shear modulus, engineering strain, failure stress, failure strain, flexural creep stiffness, flexural creep compliance, logarithmic creep, and viscosity.

Loss shear modulus is the ratio calculated by dividing the absolute value of the peak-to-peak shear stress, by the absolute value of the peak-to-peak shear strain.

Storage shear modulus is the complex shear modulus multiplied by the cosine of the phase angle expressed in degrees. It represents the in-phase component of the complex modulus that is a measure of the energy stored during a loading cycle.

Engineering strain refers to the axial strain resulting from the application of a tensile load and calculated as the change in length caused by the application of the tensile load divided by the original unloaded length of the specimen without any correction for reduction in cross-section.

Failure stress is the tensile stress on the test specimen when the load reaches a maximum value during the test method specified in a particular standard.

Failure strain is the tensile strain corresponding to the failure stress.

Flexural creep stiffness is the ratio obtained by dividing the maximum bending stress in the bending beam rheometer by the maximum bending stress.

Flexural creep compliance is the ratio obtained by dividing the maximum bending strain in the bending beam rheometer by the maximum bending stress.

Logarithmic creep (m value) is the absolute slope of the logarithm of the stiffness curve versus the logarithm of time.

Viscosity is the resistance to flow of a liquid substance.

Accordingly, it is an object of the present invention to provide an asphalt stability test vessel which recreates the conditions of modified asphalt binder in the field.

It is a further object of the present invention to provide a laboratory asphalt stability test which adds the variable of agitation to test modified asphalt binder.

It is yet a further object of the present invention to provide a laboratory asphalt stability test which does not require freezing of the modified asphalt binder.

It is yet a further object of the present invention to provide a laboratory asphalt stability test which may be economically administered.

Finally, it is another object of the present invention to provide a laboratory asphalt stability test which can be easily administered in the field.

These and additional objects, advantages, features and benefits of the present invention will become apparent from the following specification.

DETAILED DESCRIPTION OF THE PREFERRED EMBODIMENTS

Figure 1:
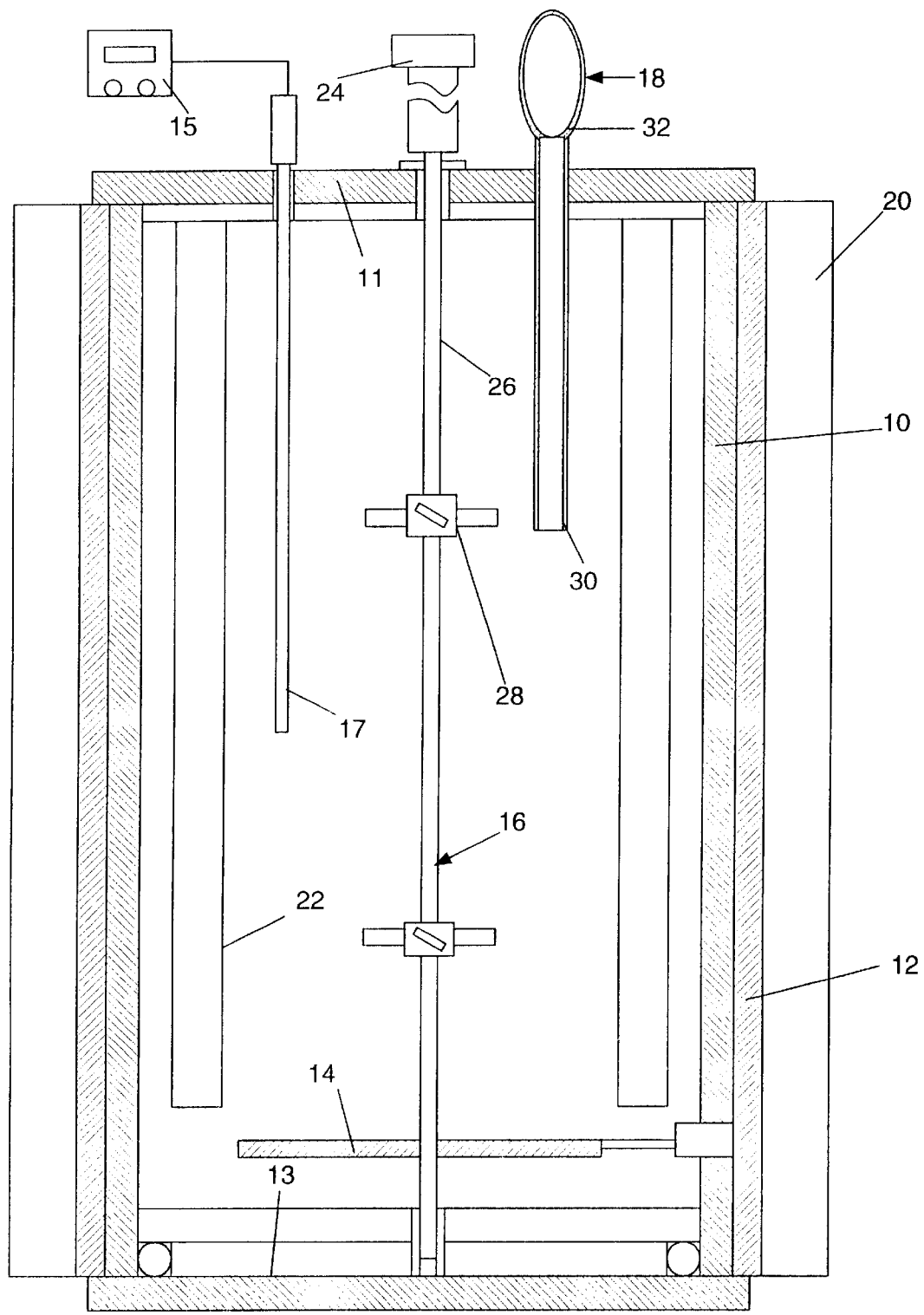
FIG. 1 is a cross-sectional view of a asphalt stability test vessel in accordance with the present invention.
Figure 2:
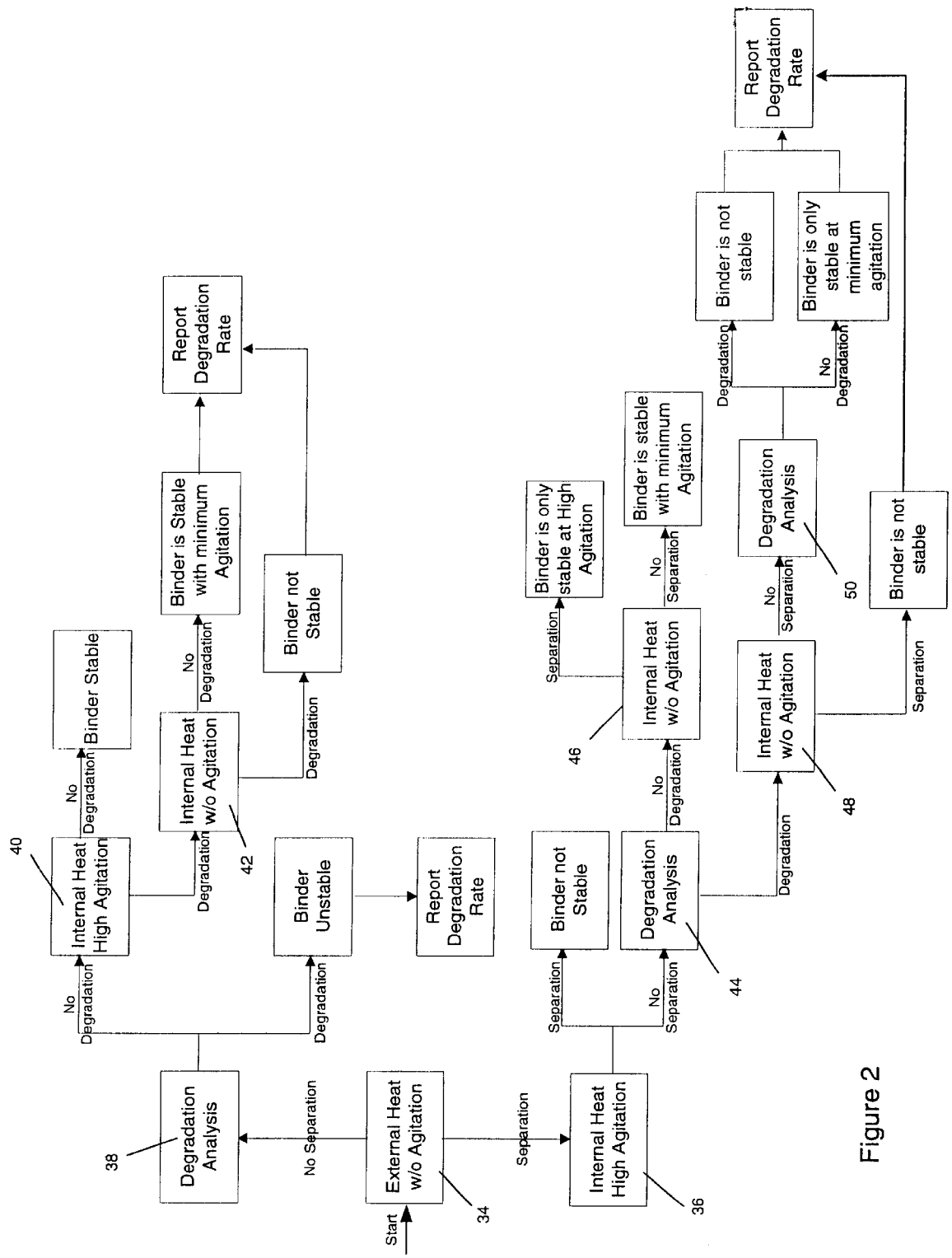
FIG. 2 is a flow chart of the complete laboratory asphalt stability test in accordance with the present invention.

With reference now to the drawings, and particularly to FIG. 1, there is shown a cross sectional view of an asphalt stability test vessel 1. The asphalt stability test vessel 1 includes a container 10, an external heater 12, an internal heater 14, an agitator assembly 16, a temperature controller 15, and at least one sampling tube 18. The external heater 12 is disposed on the outside surface area of the container 10. The external heater 12 is surrounded by a thermal insulator 20 such as fiberglass. The internal heater 14 is preferably disposed inside the container and at substantially the bottom thereof. The internal heater 14 may also be located in any area such that the asphalt is heated satisfactorily. A plurality of baffles 22 extend vertical downward from a top 11 of the container 10. The agitator assembly 16 includes a motor 24, a shaft 26, and at least one propeller 28. The shaft 16 is pivotally mounted to the top 11 and a bottom 13 of the container 10. The motor 24 is mounted to the top 11 of the container 10 and drives the shaft 26 which has at least one propeller 28 attached thereto. The speed of the motor 24 is preferably adjustable.

The top 11 of the container 10 has an opening for the insertion of a temperature probe 17. The temperature controller 15 is mounted to the top 11 of the container. The temperature probe 17 extends downward from the temperature controller 15 and is preferably disposed in substantially the middle of the container 10. The top 11 of the container 10 has at least one opening for the insertion of the sampling tube 18. The sampling tube 18 includes a tube 30 and a bulb 32. To obtain a sample of modified asphalt binder from the container 10, the sampling tube 18 is inserted into the container 10 and the bulb 32 is squeezed. A small amount of asphalt will be held by in the tube 30 for testing. A sampling tube exists for taking samples of the modified asphalt binder at substantially the top of the container 10 and also at substantially the bottom of the container 10.

The asphalt stability testing vessel 1 is a specially designed lab version of a production asphalt storage tank. Instead of having a 20,000 gallon capacity, the container 10 has a preferable capacity of approximately 1 quart. The asphalt stability testing vessel 1 has internal heating, external heating, and at least one mixing propeller similar to the production unit. The asphalt stability testing vessel has at least one propeller which is rotated at preferably 2,100 rpm for high agitation testing.

The asphalt stability testing vessel 1 is used to prepare modified asphalt binder for numerous stability tests. The stability test is started by heating preferably one quart of modified asphalt binder to a temperature of 165 degrees celsius. The sampling tubes are pre-heated in an oven to a temperature of 165 degrees celsius. The bulb 32 is removed from the tube 30 before pre-heating and added when sampling is conducted.

In box 34 of the test, the external heater 12 of the asphalt stability testing vessel 1 is turned on such that a temperature of 165 degrees celsius is maintained utilizing the temperature controller 15. Preferably, one quart of heated modified asphalt binder is poured into the asphalt stability testing vessel 1. After the temperature has stabilized to 165 degrees celsius, timing is started. The top and bottom thirds of the vessel are twice sampled with the sampling tube 18. Sampling occurs at 0, 3, 6, 12, 24 and 48 hours after temperature stabilization. The contents of the sampling tube 18 are discharged into silicon molds. The samples are then removed from the silicon molds and placed into a rheometer. The complex shear modulus (G*) and the phase angle (δ) are tested by the rheometer.

To determine separation, the complex shear modulus (G*) of the top sample is divided by the complex shear modulus (G*) of the bottom sample for time periods 0, 3, 6, 12, 24, and 24 hours. The phase angle (δ) of the top sample is divided by the phase angle (δ) of the bottom sample for time periods 0, 3, 6, 12, 24, and 24 hours. If any G* Ratio of 0, 3, 6, 12, 24, or 48 hours exceeds 1.2 or falls below 0.8, separation has occurred. If any δ Ratio of 0, 3, 6, 12, 24, or 48 exceeds 1.2 or falls below 0.8, separation has occurred. If separation occurs, a new sample is tested utilizing the internal heating and high agitation of the asphalt stability testing vessel 1 in box 36. If no separation occurs, the values obtained in box 34 are subjected to degradation analysis in box 38.

Degradation is determined by calculating complex shear modulus (G*) and the phase angle (δ) ratios.

$$G* \text{ Ratio} = (G*_{top} + G*_{bot})/2(G*_{initial})$$

$$\delta \text{Ratio} = (\delta_{top} + \delta_{bot})/2(\delta_{initial})$$

Where:

$G*_{initial}$: average of the top and bottom samplings at 0 hours.

$G*_{top}$: average of the two samplings taken at each sampling time 3, 6, 12, 24 and 48 hours.

$G*_{bot}$: average of the two samplings taken at each sampling time 3, 6, 12, 24, and 48 hours.

$\delta_{initial}$: average of the top and bottom samplings at 0 hours.

$\delta_{top}$: average of the two samplings taken at each sampling time 3, 6, 12, 24 and 48 hours.

$\delta_{bot}$: average of the two samplings taken at each sampling time 3, 6, 12, 24, and 48 hours.

If any G* Ratio of 3, 6, 12, 24, or 48 hours exceeds 1.2 or falls below 0.8, degradation has occurred. If any δ Ratio of 3, 6, 12, 24, or 48 exceeds 1.2 or falls below 0.8, degradation has occurred. If degradation has occurred the binder is unstable. If no degradation has occurred, modified asphalt binder is tested in box 40 by internal heating and high agitation.

In box 40 of the test, the internal heater 14 of the asphalt stability testing vessel 1 is turned on such that a temperature of 165 degrees celsius is maintained using the temperature controller 15. The propellers of the asphalt stability testing vessel 1 rotate at a preferable speed of 2100 rpm. Preferably, one quart of heated modified asphalt binder is poured into the asphalt stability testing vessel 1. After the temperature has stabilized to 165 degrees celsius, timing is started. The top and bottom thirds of the vessel are twice sampled with a sampling tube 18. Sampling occurs at 0, 3, 6, 12, 24 and 48 hours after temperature stabilization. The contents of the sampling tube are discharged into silicon molds. The samples are then removed from the silicon molds and placed into a rheometer. The complex shear modulus (G*) and the phase angle (δ) are test by the rheometer.

The values of complex shear modulus and phase angle obtained in box 40 are subjected to degradation analysis similar to that disclosed in box 38. If no degradation occurs, the binder is stable. If degradation occurs, a new test is conducted in box 42. The test in box 42 is similar to the test in box 40 with the exception that the propeller does not rotate. New samples are extracted at 0, 3, 6, 12, 24, and 48 hours and tested utilizing a rheometer. Next, the values of complex shear modulus (G*) and phase angle (δ) obtained in box 42 are subjected to degradation analysis similar to that of box 38. If degradation occurs the binder is not stable. If no degradation occurs binder is stable only with minimum agitation.

Next, the values of complex shear modulus and phase angle obtained in box 36 are subjected to separation analysis. If separation has occurred after box 36, the binder is not stable. If no separation has occurred after box 36, the values obtained in box 36 are subjected to degradation analysis in box 44. If no degradation occurs, new samples are taken in box 46 after being subjected to internal heating without agitation. The values obtained in box 46 are subjected to separation analysis. If separation has occurred, the binder is stable only at high agitation. If no separation has occurred, the binder is stable with minimum agitation.

If degradation occurs in box 44, new samples are tested utilizing internal heating without agitation in box 48. After the test in box 48 is performed, the values obtained in box 48 are subjected to separation analysis. If separation occurs, the binder is not stable. If no separation occurs, the values obtained in box 48 are subjected to degradation analysis in box 50. If degradation occurs the binder is not stable. If no degradation occurs, the binder is stable only at minimum agitation.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A method for testing asphalt for separation and degradation characteristics, wherein separation is characterized by division of the asphalt into its components and degradation is characterized by the deterioration of asphalt components and/or any bonding therebetween, the method comprising:
   (a) adding asphalt into a container allowing external heating of asphalt within the container, internal heating of asphalt within the container, and agitation of asphalt within the container;
   (b) applying external heating to the asphalt within the container with no agitation;
   (c) testing the asphalt of step (b) for separation;
   (d) applying internal heating to the asphalt within the container with agitation;
   (e) testing the asphalt of step (d) for degradation;
   (f) if the asphalt of step (d) has degraded:
      (i) applying internal heating to the asphalt within the container with no agitation, and
      (ii) testing the asphalt of step (i) for separation and/or degradation.

2. The method of claim 1 further comprising the step of testing the asphalt of step (b) for degradation.

3. The method of claim 1 wherein if the asphalt of step (d) has not degraded, the following steps are performed:
   (g) applying internal heating to the asphalt within the container with no agitation, and
   (h) testing the asphalt of step (g) for separation.

4. The method of claim 1 further comprising the step of testing the asphalt of step (d) for separation.

5. The method of claim 1 wherein the separation tests are performed by comparing characteristics of asphalt samples obtained from different heights within the container.

6. The method of claim 1 wherein the degradation tests are performed by comparing characteristics of asphalt samples obtained at different times within the container.

7. The method of claim 1 wherein the degradation tests are performed by comparing characteristics of asphalt samples obtained at different times within the container and also at different heights within the container.

8. A method for testing asphalt for separation and degradation characteristics, wherein separation is characterized by division of the asphalt into its components and degradation is characterized by the deterioration of asphalt components and/or any bonding therebetween, the method comprising:
(a) adding asphalt into a container allowing external heating of asphalt within the container, internal heating of asphalt within the container, and agitation of asphalt within the container;
(b) applying external heating to the asphalt within the container with no agitation;
(c) testing the asphalt of step (b) for separation,
(d) applying internal heating to the asphalt within the container with agitation;
wherein:
(i) if separation is found in step (c), the asphalt is tested for separation after each subsequent application of internal or external heat;
(ii) if no separation is found in step (c), the asphalt is tested for degradation after each subsequent application of internal or external heat.

9. The method of claim 8 further comprising the step of:
(e) after step (d), applying internal heating to the asphalt within the container with no agitation.

10. The method of claim 8 wherein the separation tests are performed by comparing characteristics of asphalt samples obtained from different heights within the container.

11. The method of claim 8 wherein the degradation tests are performed by comparing characteristics of asphalt samples obtained at different times within the container.

12. The method of claim 8 wherein the degradation tests are performed by comparing characteristics of asphalt samples obtained at different times within the container and also at different heights within the container.

13. A method for testing asphalt for separation and degradation characteristics, wherein separation is characterized by division of the asphalt into its components and degradation is characterized by the deterioration of asphalt components and/or any bonding therebetween, the method comprising:
(a) adding asphalt into a container allowing external heating of asphalt within the container, internal heating of asphalt within the container, and agitation of asphalt within the container;
(b) subjecting the asphalt to a first combination of conditions including
(i) internal or external heating, and
(ii) agitation or no agitation, for an interval of time;
(c) measuring the degradation of the asphalt of step (b) by comparing its properties at different times within the time interval.

14. The method of claim 13 wherein the compared properties include complex shear modulus.

15. The method of claim 13 wherein the compared properties include phase angle.

16. The method of claim 13 wherein the compared properties include complex shear modulus and phase angle.

17. The method of claim 13 wherein degradation is measured by comparing the properties of the asphalt at different times within the time interval and also at different heights within the container.

18. The method of claim 13 further comprising:
(d) subjecting the asphalt to a second combination of conditions as recited in step (b) for an interval of time, such second combination being different from the first combination; and
(e) measuring the degradation of the asphalt of step (d) by comparing its properties at different times within the time interval.

19. An asphalt stability testing vessel comprising:
(a) a container suitable for containing asphalt;
(b) at least one sampling tube for extracting samples of the asphalt from inside the container;
(c) agitator means for mixing the asphalt in the container;
(d) exterior heating means for applying external heating to the container when asphalt is therein without agitating the asphalt;
(e) separation testing means for testing the asphalt for separation;
(f) interior heating means for applying internal heating to the container when asphalt is therein while agitating the asphalt;
(g) degradation testing means for testing the asphalt for degradation;
wherein if degradation is found, internal heating may be applied to the container when asphalt is therein without agitating the asphalt.

20. The asphalt stability testing vessel of claim 19 further comprising temperature controller means for regulating the thermal output of the exterior heating means and the interior heating means.

21. The asphalt stability testing vessel of claim 19 wherein the speed of the agitator means is adjustable.

22. The asphalt stability testing vessel of claim 19:
wherein the agitator means includes a rotating shaft about which one or more propellers orbit,
and wherein the asphalt stability testing vessel further comprises at least one baffle situated within the planes in which the propellers orbit.

23. The asphalt stability testing vessel of claim 19 further comprising one or more baffles disposed within the container.

24. The asphalt stability testing vessel of claim 23 wherein the baffles are oriented vertically within the container.

25. An asphalt stability testing vessel comprising:
(a) a container having a container interior and a container exterior;
(b) agitator means for mixing asphalt within the container interior;
(c) exterior heating means for heating the asphalt from the container exterior when asphalt is within the container interior, such heating being applied without agitating the asphalt;
(d) separation testing means for testing the asphalt for separation;
(e) interior heating means for heating the asphalt from the container interior when asphalt is within the container interior, such heat being applied while agitating the asphalt;
(f) degradation testing means for testing the asphalt for degradation;
wherein if degradation is found, internal heating may be applied to the container when asphalt is therein without agitating the asphalt.

26. The asphalt stability testing vessel of claim 25 further comprising one or more baffles disposed within the container interior.

27. The asphalt stability testing vessel of claim 25 further comprising sampling means for obtaining from the container exterior discrete samples of asphalt from within the container interior.

28. The asphalt stability testing vessel of claim 27 wherein the sampling means allow sampling at different heights within the container.

29. The asphalt stability testing vessel of claim 28 wherein the internal heating means is provided at substantially the bottom of the container.

30. The asphalt stability testing vessel of claim 25 further comprising baffles oriented vertically within the container.

31. The asphalt stability testing vessel of claim 25:
wherein the agitator means includes a rotating shaft about which one or more propellers orbit,
and wherein the asphalt stability testing vessel further comprises at least one baffle situated within the planes in which the propellers orbit.

* * * * *